US00PP13753P29

(12) United States Plant Patent
Banning

(10) Patent No.: US PP13,753 P2
(45) Date of Patent: Apr. 29, 2003

(54) APPLE TREE NAMED 'BANNING GALA'

(76) Inventor: Robert Banning, 4000 Grant Rd., East Wenatchee, WA (US) 98802

( * ) Notice: Subject to any disclaimer, the term of this patent is extended or adjusted under 35 U.S.C. 154(b) by 0 days.

(21) Appl. No.: 09/963,252

(22) Filed: Sep. 25, 2001

(51) Int. Cl.[7] ..... A01H 5/00
(52) U.S. Cl. ..... Plt./162
(58) Field of Search ..... Plt./162

(56) References Cited

U.S. PATENT DOCUMENTS

PP4,121 P 10/1977 Ten Hove
PP6,172 P 5/1988 Creech
PP8,673 P 4/1994 Waliser
PP9,861 P 4/1997 Moore et al.
PP10,114 P 11/1997 Gale
PP10,840 P 3/1999 Simmons et al.

*Primary Examiner*—Bruce R. Campell
*Assistant Examiner*—Susan B McCormick
(74) *Attorney, Agent, or Firm*—Christensen O'Connor Johnson Kindness PLLC

(57) ABSTRACT

A new and distinct variety of apple tree which originated as a limb mutation of 'Imperial Gala' characterized by an intense red blush and an even darker red over-stripe at harvest maturity.

3 Drawing Sheets

LATIN NAME OF THE GENUS AND SPECIES OF THE PLANT CLAIMED

*Malus domestica.*

VARIETY DENOMINATION

'Banning Gala'

BACKGROUND OF THE INVENTION—DISCOVERY AND ASEXUAL REPRODUCTION OF THE TREE

The new variety, denominated 'Banning Gala', was discovered by Robert Banning in 1997 on a four-year old tree at his orchard at 4000 Grant Road, East Wenatchee, Wash. The tree having the limb mutation was found in a cultivated block of 'Imperial Gala' (not patented). The discovery was made at thinning time, and even at this pre-harvest stage, the fruit of the mutated limb was distinctly higher in red color than fruit on other, adjacent limbs on the original tree and on any other tree in the block.

Buds from the original limb were taken in 1998 and budded to 110 'Malling 26' rootstocks. Other trees on 'Malling 9' rootstock were top worked to the new strain the same year. In August 1999, approximately 700 trees were budded on 'Malling 26', 'Malling 7' and 'Malling 9' rootstock (third generation). Approximately 25% of the 110 trees budded in 1998 and bore fruit in 1999, with the fruit on all fruiting trees being identical to that of the original single limb mutation from the 'Imperial Gala' parent, thereby establishing the stability of the new variety.

SUMMARY OF THE TREE

The new variety has been compared to the parent tree, 'Imperial Gala', and to other 'Gala' strains as indicated below. These comparisons are from the 1999 and 2000 harvest. The data in Table 1 below was obtained from samples of the strains grown in three orchards within 10 miles of East Wenatchee, Wash., at the same elevation and growing conditions. Data on number of pickings expected are from grower testimony.

TABLE 1

Comparison of Gala strains/1

| Variety/Strain | U.S. Plant Pat. No. | % Red Color | Color Pattern | No. Picks |
|---|---|---|---|---|
| 'Banning Gala' | — | 90 | broad dark red strip, red blush | 1 |
| 'Imperial Gala' | — | 50 | strong variable-width stripe | 3 |
| 'Royal Gala' | 4121 | 50 | strong variable-width stripe | 3 |
| 'Scarlet Gala' | 6172 | 75 | weak broad stripe, pink-red blush | 2 |
| 'Crimson Gala' | 8673 | 85 | weak narrow stripe, bright pink-red blush | 2 |
| 'Pacific Gala' | 9681 | 80 | weak narrow stripe, bright pink-red blush | 2 |
| 'Gale Gala' | 10114 | 100 | narrow stripe, strong blush | 1 |
| 'Buckeye Gala' | 10840 | 100 | narrow stripe, strong blush | 1 |

BRIEF DESCRIPTION OF THE DRAWINGS

The accompanying photographs show the following characteristics of this new variety.

DETAILED BOTANICAL DESCRIPTION

Figure 1:
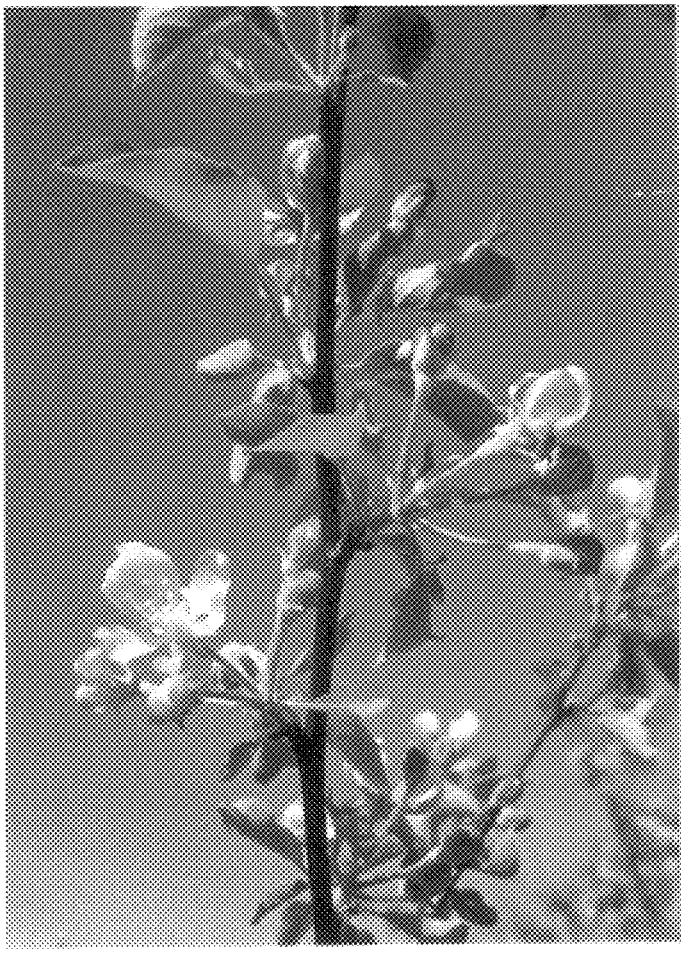
FIG. 1 shows a bloom of the new variety as observed on Apr. 24, 2000, there being no detectable difference from the parent 'Imperial Gala' or other known 'Gala' strains.
Figure 2:
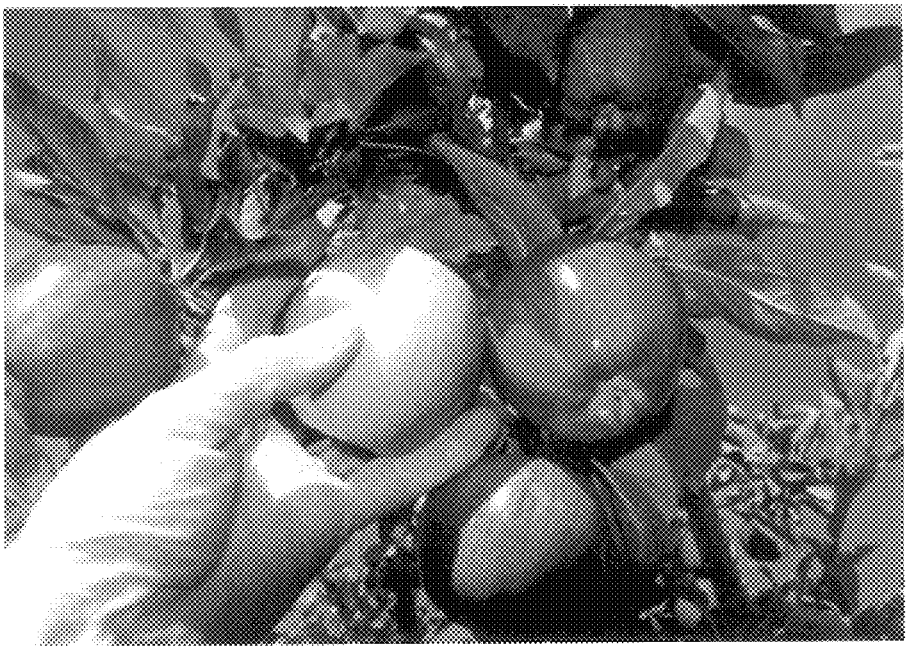
FIG. 2 shows typical fruit of the new variety on the original mutated branch with fruit of the parent held for comparison, illustrating the early red development of the new variety.
Figure 3:
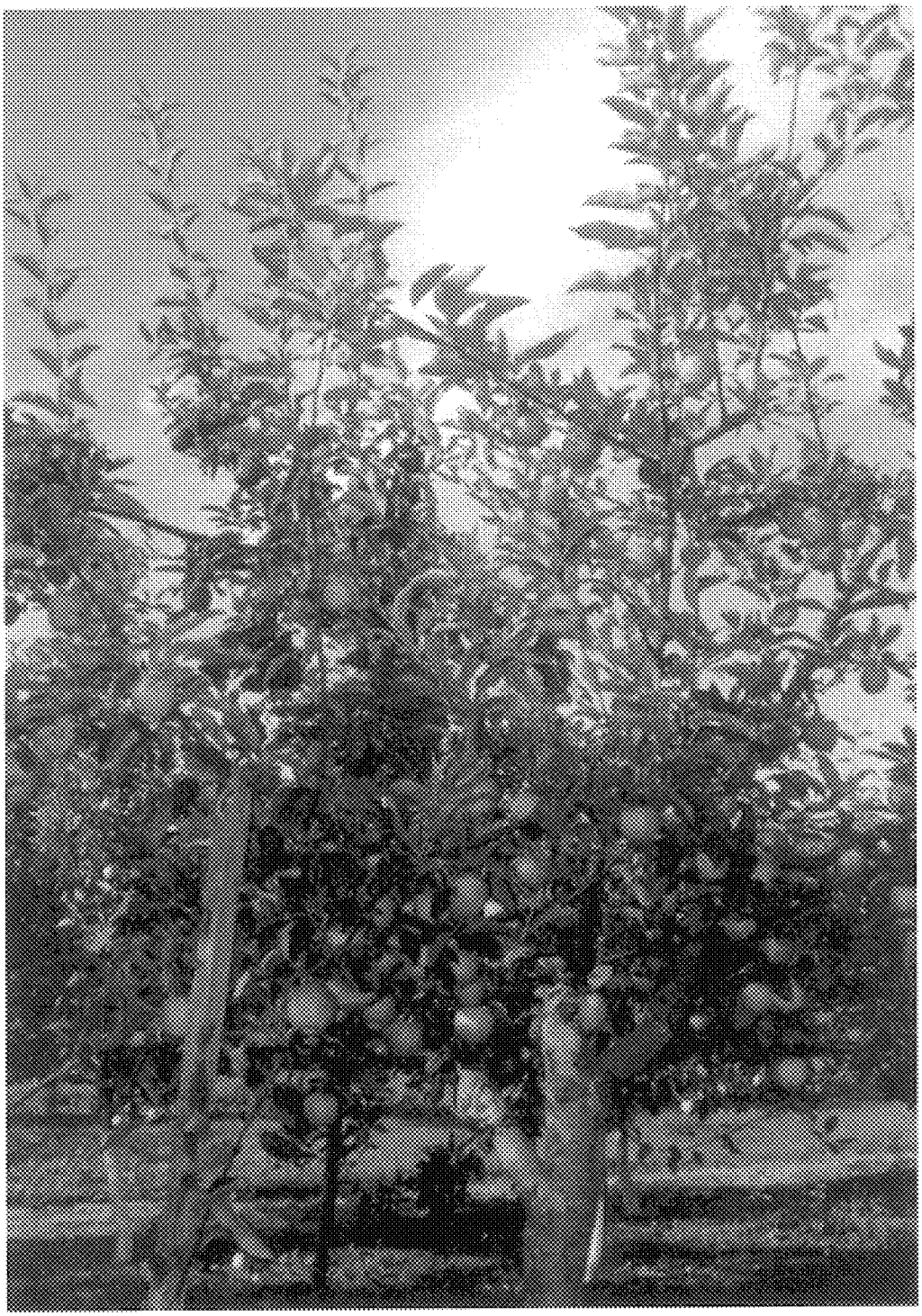
FIG. 3 shows the original parent tree with the mutated limb showing the distinctly different coloring of fruit on the mutated limb.
Figure 4:
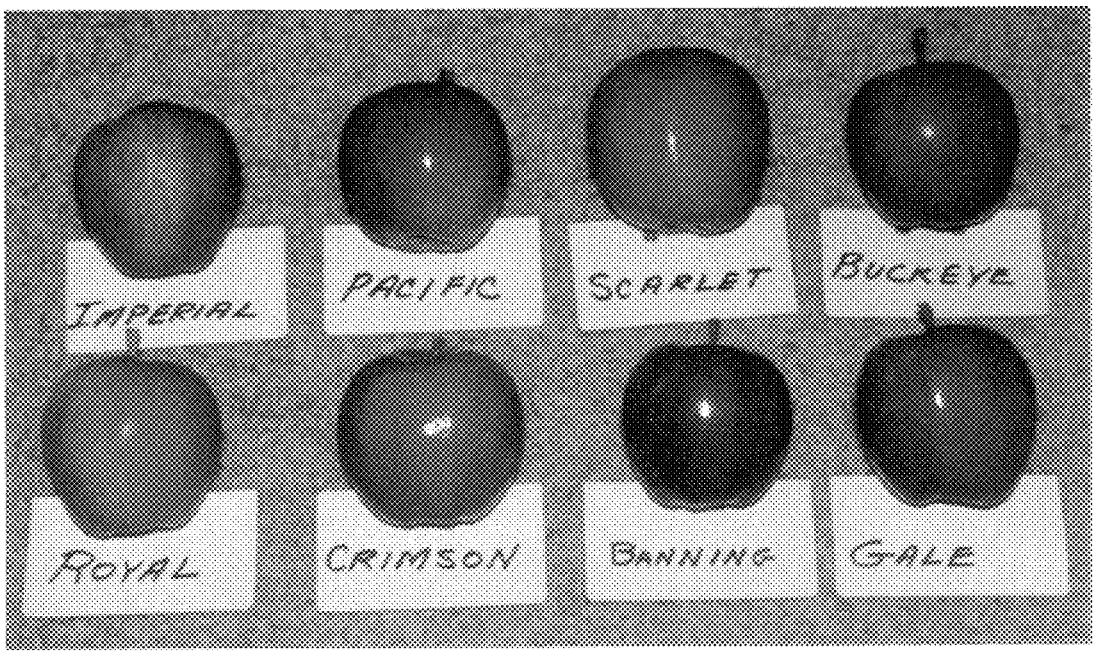
FIG. 4 shows fruit from other known 'Gala' strains, top row, left to right: 'Imperial Gala' (parent not patented), 'Pacific Gala' ('Olsentwo cv.', U.S. Plant Pat. No. 9,861), 'Scarlet Gala' ('Creech cv.', U.S. Plant Pat. No. 6,172), 'Buckeye Gala' ('Simmons cv.', U.S. Plant Pat. No. 10,840); bottom row, left to right: 'Royal Gala' ('Tenroy cv.', U.S. Plant Pat. No. 4,121), 'Crimson Gala' ('Waliser cv.', U.S. Plant Pat. No. 8,673), 'Banning Gala' (new variety), 'Gale Gala' ('Malaga cv.', U.S. Plant Pat. No. 10,114).
Figure 5:
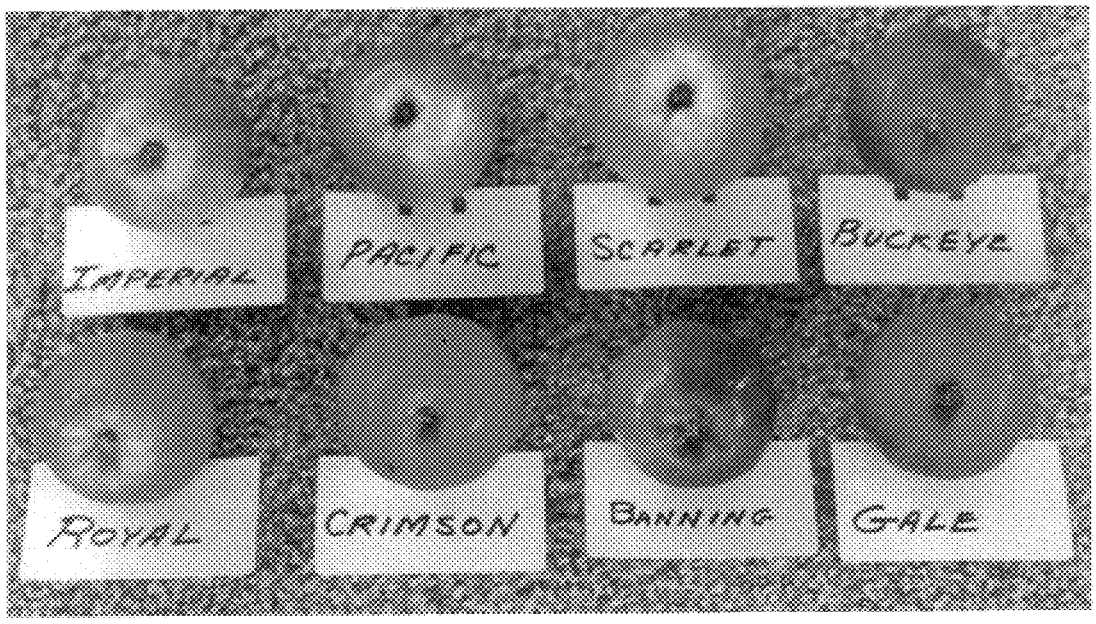
FIG. 5 shows a comparison of the new variety with other 'Gala' strains, viewing the calyx end, in the same order as FIG. 4, illustrating the deeper red color of mature fruit of the new variety.

The following detailed description of the characteristics of the new strain of 'Gala' apple is based on observations at the Banning Orchards in East Wenatchee, Wash. The observed tree, limb and leaf characteristics of the new variety are essentially identical to the parental 'Imperial Gala' variety. All color descriptions by number citations herein refer to the Munsell Book of Color, Macbeth Division, Kollmorgen Instruments Corp., 405 Little Britain road, New Winsor, N.Y. 12553.

Tree: Medium size typical of other Gala trees, semi-dwarf due to dwarfing rootstock.

*Height.*—8–10 ft.

*Width.*—7–9 ft.

*Vigor.*—Medium to high (18 to 30 inches annual growth), similar to parent; Upright to somewhat spreading.

*Trunk: Stocky; Smooth.*

*Trunk bark texture.*—Smooth on young wood, becoming flaking and rough with age.

*Trunk bark color.*—Brownish grey 10RP 5/2 .

*Average diameter of trunk on mutated branch of original tree at approximately 1.5 m above the ground in 2000.*—12 cm.

Branches: Mostly upright, angles about 60 degrees at emergence.

*Branch color.*—One-year dormant shoot 10RP 2/2; two year branch 10RP 6/2 (slightly darker than parent).

*Branch pubescence.*—Fine pubescence, grey (RP 6/10).

*Branch lenticels.*—Oval, medium density, tan (7.5YR 7/4); about 1 mm.

*Internodes.*—24.9 mm. average length on one-year old shoots.

*Average branch diameter.*—5 cm.

Leaves (primary): Broad, medium green; glossy on upper surface, finely pubescent on lower surface; oblong, acuminate.

*Base shape.*—Acute.

*Vein color.*—Light green 10GY 7/2.

*Venation pattern.*—Alternate lateral venation.

*Length.*—(Average of 10 leaves, sampled September 1999 at Banning orchard) from 72 to 115 mm.; average 94.7 mm.

*Width.*—Measured as above, from 41 to 75 mm.; average 54.3 mm.

*Petiole.*—22 to 37 mm.; average 26 mm. (1.5 mm. average diameter).

*Margin.*—Finely serrate.

*Tip.*—Acuminate.

*Stipules.*—In pairs, thin, pointed, 11 to 20 mm. in length; 1 to 3 mm. in width.

*Color.*—Upper surface 2.5GY 5/4. Lower surface 2.5GY 6/4. Petiole 10RP 4/6.

*Pubescence.*—Upper surface glabrous, with some pubescence along midrib; lower surface fine pubescence over entire surface; greyish color RP 8/10.

Flowers:

*Bud.*—Round to oval, approximately 10 mm. in length and 5 mm. in diameter.

*First bloom.*—Apr. 17, 2000, at East Wenatchee, Wash.

*Full bloom.*—Apr. 27, 2000, at East Wenatchee, Wash.

*Bloom duration.*—Approximately 18 days.

*Size.*—Large, 52–60 mm.

*Color.*—Pink in bud stage, to white in full flower; bud color 2.5T 7/6.

*Petals.*—5 in number, rounded at apex and acuminate at base, with a smooth margin and texture, position of margins is touching to overlapping.

*Stamen.*—Single row, anthers bright yellow 2.5Y 3.5/12.

*Pistil.*—Stigma medium length, branched at top into 5 elements; styles medium.

*Sepals.*—5 in number, 12 mm. long×5 mm. wide at base, pubescent; tapering to a point, recurved downward, pale green 10GY 7/2.

*Peduncle.*—Approximately 20 mm.. in length (range of 12–25 mm.), 1–2 mm. in diameter, pale green 10GY 7/2.

*Pollination requirements.*—Compatible with all diploid cultivars that bloom at the same time except Gala; as with other Gala strains, it is less compatible with Golden Delicious.

*Fragrance.*—Light.

Fruit: Maturity when described was early harvest period (Aug. 28, 2000).

*Firmness.*—19 pounds.

*Soluble solids.*—12.4%.

*Starch index.*—(1 to 6 scale) 2.5.

*Acid content.*—0.5% malic acid.

*Storage.*—Samples were stored until May 2001 in common storage (0 to 2° C.), where they remained in good condition, comparable to other 'Gala' varieties.

*Size.*—Medium (65 mm. to 80 mm. transverse diameter, 70 mm. length).

*Form.*—Conic, symmetric; length/diameter ratio approximately 1.05, with ribbing absent, but with 5 small lobes at the calyx end.

*Stem cavity.*—Narrow, medium depth (17 mm.).

*Basin cavity.*—Medium depth (10 mm.), medium width (30 mm.), lightly pubescent.

*Stem.*—Medium length (25 to 27 mm.); medium thickness (3 to 4 mm.).

*Locules (carpels).*—Large, 5 in number, open with seeds loosely attached.

*Skin.*—Medium thickness, tender, glossy, no tendency to become oily in storage, not prone to russet, some cracking around stem cavity as fruit becomes overmature.

*Lenticels.*—5Y 9/4, small, oblong, conspicuous.

*General color effect.*—Combination of striped and blushed red color over 90% of fruit surface: See Table 1 for comparison with other Gala strains.

*Ground color.*—Greenish yellow 7.5Y 7/8 at early picking maturity (Aug. 28, 2000).

*Overcolor.*—Prominent stripe, 7.5R 3/10 over a lighter blush (7.5R 4/4).

*Russet.*—Generally absent, unless caused by caustic sprays or weather conditions.

*Flesh.*—10Y 9/4; juicy, sweet, soluble solids 12 to 15%, non-stringent, sprightly flavor; low acidity, approximately 0.4% to 0.5% malic acid; low aroma; firmness 19 pounds at first harvest; starch level 2.5/6.0.

*Core.*—Bundle area round, average width of core 26 mm., average length 23 mm., 10 bundles; core lines prominent; locules open; calyx tube fairly long (15 mm.), closed.

*Seeds.*—Mostly 2 per cell; obovate; color 7.5YR 5/4 (light brown); length 9 mm.×5 mm. width; loosely adhering to the carpel wall.

*Usage.*—primarily fresh eating (dessert); can be used for culinary purposes; requires less sugar than most other varieties.

I claim:

1. A new and distinct variety of apple tree as herein shown and described.

* * * * *